United States Patent [19]

Takaishi et al.

[11] Patent Number: 4,698,435
[45] Date of Patent: Oct. 6, 1987

[54] PROCESS FOR PREPARING 3-PHENACYLIDENE PHTHALIDES

[75] Inventors: Naotake Takaishi; Kimihiko Hori, both of Utsunomiya, Japan

[73] Assignee: Kao Corporation, Tokyo, Japan

[21] Appl. No.: 909,297

[22] Filed: Sep. 19, 1986

[30] Foreign Application Priority Data

Oct. 8, 1985 [JP] Japan .................. 60-224095

[51] Int. Cl.$^4$ ......................... C07D 307/88
[52] U.S. Cl. .................................. 549/305
[58] Field of Search ......................... 549/305

[56] References Cited

U.S. PATENT DOCUMENTS 4,182,622 1/1980 Houbion et al. ............... 549/305
4,255,181 3/1981 Houbion et al. ............... 71/88

OTHER PUBLICATIONS

Knight et al., CA 82(25) 170544r.

Primary Examiner—Jane T. Fan

Attorney, Agent, or Firm—Oblon, Fisher, Spivak, McClelland & Maier

[57] ABSTRACT

A novel process for preparing a 3-phenacylidene phthalide of the general formula (II)

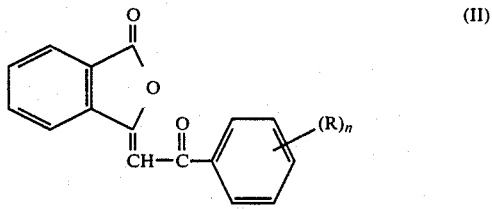

which comprises reacting a halogenating reagent with a 2-carboxydibenzoylmethane.

The 2-carboxydibenzoylmethane can be inexpensively prepared, so that the 3-phenacylidene phthalides which are useful as a growth regulant for plants and a safering agent to reduce herbicidal injury to plants can be readily obtained economically in high yield.

1 Claim, No Drawings

PROCESS FOR PREPARING 3-PHENACYLIDENE PHTHALIDES

BACKGROUND OF THE INVENTION

1. Field of the Invention

This invention relates to a process for preparing 3-phenacylidene phthalides useful as growth regulants for plants and safering agents to reduce herbicidal injury to plants.

2. Description of the Prior Art

3-Phenacylidene phthalides are known to have various effects on plants. For instance, according to B. T. Brown and G. F. Katekar et al, it has been reported that the phthalides act to inhibit root geotropism of cress and rygrass seedlings [Experientia, 28, 1290 (1972); Pesticide Science, 4, 473 (1973); Phytochemistry, 15, 1421 (1976); Plant Physiology, 68, 1460 (1981)]. J. A. Hubion et al reported that the phthalides have utility as a growth regulants [U.S. Pat. No. 4,255,181 (1981)] and utility as safering agents to reduce herbicidal injury to plants [U.S. Pat. No. 4,182,622 (1980)].

For the preparation of 3-phenacylidene phthalides, there are known processes using the following reaction sequences (1) and (2) (described in the above literature) and (3) a process set forth in Journal of Chemical Society, Perkins Transaction I, 635 (1975).

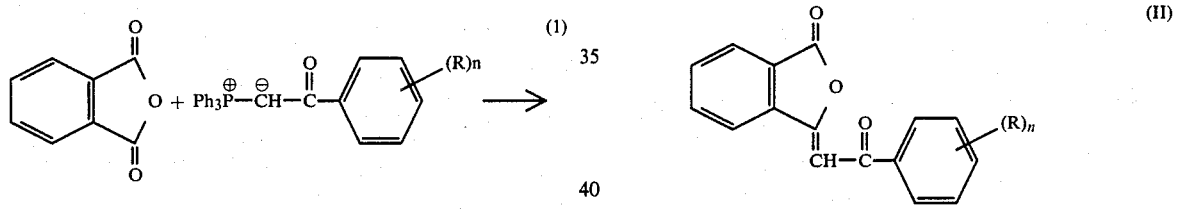
(1)

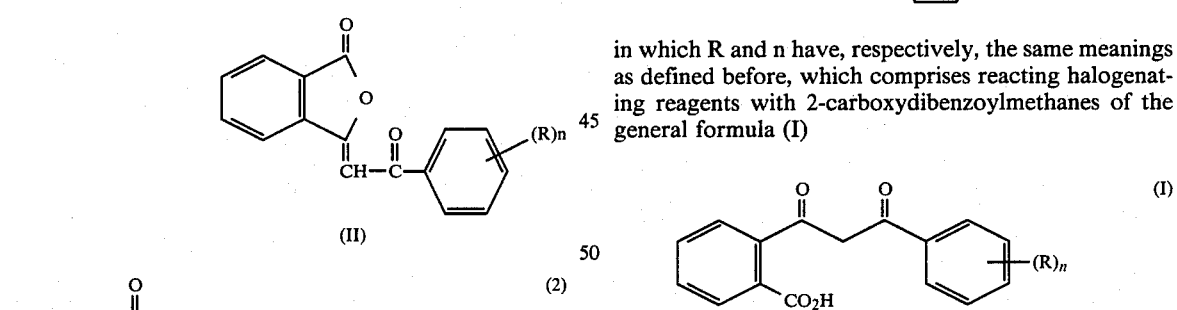
(2)

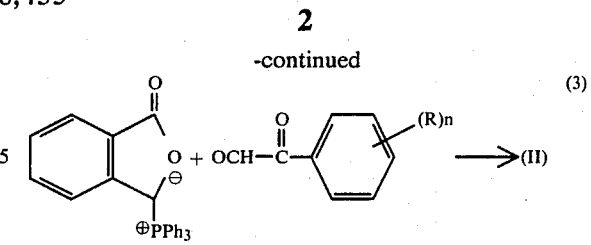
(3)

in which Rs are substituents capable of substitution at any position of the benzene nucleus and may be different or the same, and represent a hydrogen atom, a halogen atom or a linear or branched alkyl, alkenyl or alkoxy group having from 1 to 18 carbon atoms, and n is an integer of from 1 to 5.

However, all these processes require expensive staring materials and also skills in proceeding reaction and are not adapted for the preparation of the phthalides in large amounts.

SUMMARY OF THE INVENTION

The present inventors have made intensive studies on the preparation of the phenacylidene phthalides and found that 3-phenacylidene phthalides (II) can be readily prepared from 2-carboxydibenzoylmethanes which can be inexpensively prepared. The present invention was accomplished on the basis of the above finding.

According to the invention, there is provided a process for preparing 3-phenyacylidene phthalides of the general formula (II)

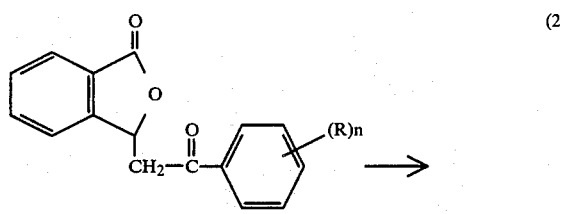
(II)

in which R and n have, respectively, the same meanings as defined before, which comprises reacting halogenating reagents with 2-carboxydibenzoylmethanes of the general formula (I)

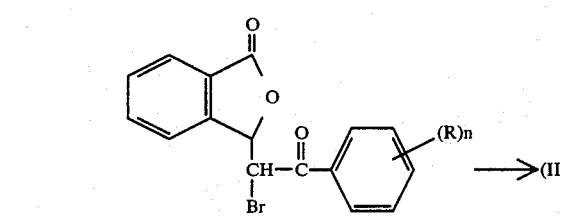
(I)

in which R and n have, respectively, the same meanings as defined before.

DETAILED DESCRIPTION OF THE INVENTION AND PREFERRED EMBODIMENTS

In the compounds of the formulae (I) and (II), the linear or branched alkyl group having from 1 to 18 carbon atoms and represented by R includes, for example, methyl, ethyl, n-propyl, iso-propyl, n-butyl, t-butyl, 2-ethylhexyl, octyl, decyl, octadecyl or the like; the alkenyl group includes, for example, vinyl, allyl, isopropenyl, 10-undecenyl or the like; and the alkoxy group includes methoxy, ethoxy, n-propoxy, iso-propoxy, allyloxy, n-butoxy, t-butoxy, iso-pentyloxy, 2-ethylhexyloxy, oxtadecyloxy or the like. Examples of the halogen atom include a chlorine atom, a bromine atom, an iodine atom and the like.

In order to carry out the process of the invention, 2-carboxydibenzoylmethanes (I) and halogenating reagents are reacted in the absence of a solvent or in an inert solvent for the reaction at a temperature of −10° to 200° C., preferably from 50° to 150° C. The halogenating reagents include thionyl chloride, thionyl bromide, chlorine, bromine, iodine, phosphorus trichloride, phosphorus tribromide and the like, of which thionyl chloride or thionyl bromide is preferred. The amount of the halogenating reagents is from 1 to 10, preferably from 1.5 to 2.5, equimolar to 2-carboxy-dibenzoylmethanes (I). As a reaction solvent, chloroform, dichloromethane and the like are preferred.

Although the starting 2-carboxydibenzoylmethanes (I) of the invention are obtained by a known method [B. T. Brown et al, Pesticide Science, 4, 473 (1973)] in which phthalic diesters and acetophenones are reacted, it is preferred that phthalic anhydride and acetophenones are reacted in the presence of a base.

According to the invention, 3-phenacylidene phthalides can be readily obtained economically in high yield.

The present invention is described by way of examples.

EXAMPLE 1

3-(4'-Methoxyphenacylidene)phthalide

4'-Methoxy-2-carboxydibenzoylmethane (100 g, 0.34 mol) was added to dichloromethane (400 ml). Thionyl chloride (60.94 g, 0.51 mol) was added to the resulting suspension and the solution was stirred at 30° C. for 1 hour and further stirred at a refluxing temperature for 3 hours to complete the reaction.

The reaction mixture was subjected to distillation under reduced pressure to remove the solvent and excess thionyl chloride to give intended 3-(4'-methoxyphenacylidene)phthalide (a mixture of Z and E isomers) in an almost quantitative yield. The ratio between the Z and E isomers was determined by integration of each olefinic proton's peak area in the NMR spectrum and found to be 30:70. Thus, the E isomer was produced in a larger amount.

The mixture was washed with hot acetone to give a substantially pure E isomer in the form of yellow needles. The yield was 65% and the melting point was from 163° to 164° C.

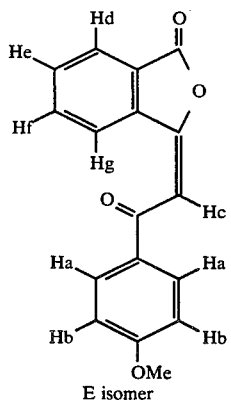
E isomer

NMR (CDCl$_3$) δ 3.91 (3H, s, —OCH$_3$) 7.00 (2H, α, J=8.5 Hz, aromatic Hb) 7.19 (1H, s, olefinic Hc) 7.67–7.88 (2H, m, aromatic He, Hf) 7.95–8.02 (1H, m, aromatic Hd) 8.04 (2H, d, J=8.5 Hz, aromatic Ha) 9.00 (1H, d, J=8.1 Hz, aromatic Hg).

IR νmax (KBr) cm$^{-1}$ 1795, 1660, 1605, 1510, 1470, 1420, 1395, 1310, 1255, 1180, 1065, 975.

The compound dissloved in the hot acetone was subjected to column chromatography on silica gel for purification to give a pure Z isomer as yellow needles. The yield was 28% and the melting point was from 172° to 173° C.

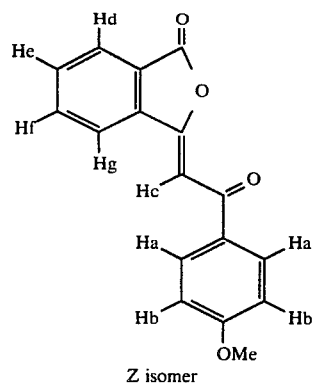
Z isomer

NMR (CDCl$_3$) δ 3.89 (3H, s, —OCH$_3$) 6.72 (1H, s, olefinic Hc) 6.93–7.03 (2H, m, aromatic Hb) 7.66–7.91 (3H, m, aromatic He, Hf, Hg) 7.94–8.05 (3H, m, aromatic Ha, Hd).

IR νmax (KBr) cm$^{-1}$ 1795, 1670, 1615, 1590, 1510, 1470, 1365, 1330, 1300, 1260, 1220, 1165, 1080, 1005, 965.

EXAMPLE 2

3-Phenacylidene phthalide

2-Carboxydibenzoylmethane (10 g, 37 mmol) was treated with thionyl chloride (8.9 g, 75 mmol) to give intended 3-phenacylidene phthalide in the same manner as in Example 1. The ratio between the E and Z isomers was determined by integration of each olefinic proton's peak area in the NMR spectrum and found to be about 50:50.

The separation between the E and Z isomers was effected using column chromatography on silica gel (elute: chloroform) to give E isomer in the form of fine yellow needles and Z isomer in the form of fine yellow prisms.

(E isomer) 4.5 g, yield: 48%. m.p. 116°–117° C.

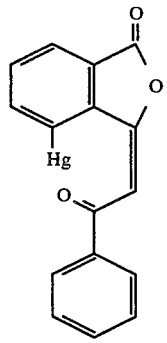

NMR (CDCl$_3$) δ 7.21 (1H, s, olefinic) 7.48–8.11 (8H, m, aromatic) 9.03 (1H, d, J=8.1 Hz, aromatic Hg).

IR νmax (KBr) cm⁻¹ 1795, 1665, 1610, 1470, 1445, 1380, 1250, 970.

(Z isomer) 4.1 g, yield: 44%. m.p. 165°–167° C.

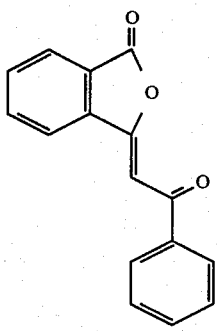

NMR (CDCl₃) δ 6.78 (1H, s, olefinic) 7.42–8.08 (9H, m, aromatic).

IR νmax (KBr) cm⁻¹ 1795, 1685, 1650, 1480, 1460, 1340, 1225, 1090, 985.

EXAMPLE 3

3-(4'-Methylphenacylidene)phthalide

4'-Methyl-2-carboxydibenzoylmethane (10 g, 35 mmol) was treated with thionyl chloride (8.4 g, 71 mmol) to give intended 3-(4'-methylphenacylidene)phthalide in the same manner as in Example 1. The ratio between the E and Z isomers was determined by integration of each olefinic proton's peak area in the NMR spectrum and found to be 30:70 with the E isomer being produced in a larger amount.

The separation between the E and Z isomers was effected using column chromatography on silica gel (elute: chloroform) to give yellow prisms of the respective products.

(E isomer) 5.6 g, yield: 60%. m.p. 205°–207° C.

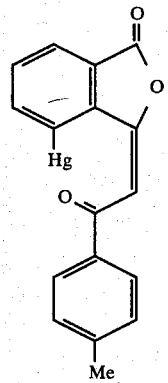

NMR (CDCl₃) δ 2.45 (3H, s, —CH₃) 7.20 (1H, s, olefinic) 7.33 (2H, d, J=8.1 Hz, aromatic) 7.66–8.09 (5H, m, aromatic) 9.02 (1H, d, J=7.7 Hz, aromatic Hg).

IR νmax (KBr) cm⁻¹ 1795, 1675, 1630, 1480, 1420, 1380, 1350, 1340, 1320, 1290, 1235, 1215, 1190, 1100, 980.

(Z isomer) 3.0 g, yield: 32%. m.p. 205°–207° C.

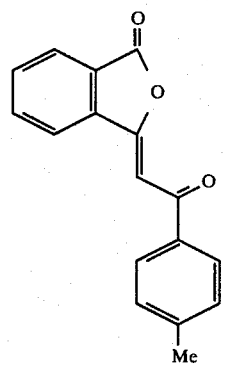

NMR (CDCl₃) δ 2.43 (3H, s, —CH₃) 6.76 (1H, s, olefinic) 7.29 (2H, d, J=8.4 Hz, aromatic) 7.60–8.06 (6H, m, aromatic)

IR νmax (KBr) cm⁻¹ 1795, 1680, 1630, 1485, 1420, 1390, 1355, 1340, 1320, 1290, 1240, 1220, 1195, 1100, 975.

What is claimed is:

1. A process for preparing a 3-phenacylidene phthalide of the formula (II)

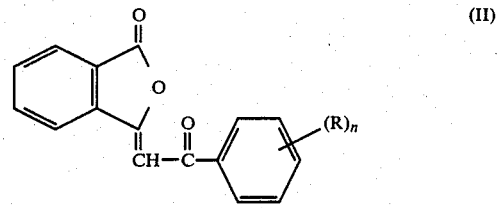

in which (R)ₙ are each a substituent capable of substitution at any position of the benzene nucleus and may be different or the same, and independently represent a hydrogen atom, a halogen atom or a linear or branched alkyl, alkenyl or alkoxy group having from 1 to 18 carbon atoms, and n is an integer of from 1 to 5, which comprises reacting a halogenating reagent with a 2-carboxydibenzoylmethane of the formula (I)

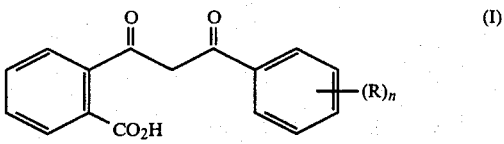

in which R and n have, respectively, the same meanings as defined above.

* * * * *